United States Patent [19]

Mizuno et al.

[11] Patent Number: 5,250,739

[45] Date of Patent: Oct. 5, 1993

[54] PROCESS FOR CATALYTICALLY OXIDIZING CYCLOOLEFINS, PARTICULARLY CYCLOHEXENE

[75] Inventors: Noritaka Mizuno, Sapporo, Japan; David K. Lyon, Bend; Richard G. Finke, Eugene, both of Oreg.

[73] Assignee: Catalytica, Inc., Mountain View, Calif.

[21] Appl. No.: 854,552

[22] Filed: Mar. 20, 1992

[51] Int. Cl.[5] .............................................. C07C 45/34
[52] U.S. Cl. ....................................... 568/360; 568/825
[58] Field of Search ................ 568/360, 400, 401, 825

[56] References Cited

U.S. PATENT DOCUMENTS

| | | | |
|---|---|---|---|
| 3,946,081 | 3/1976 | Wedemeyer et al. | 568/360 |
| 4,560,804 | 12/1985 | Veh et al. | 568/360 |
| 4,723,041 | 2/1988 | Vasilevskis et al. | 568/360 |
| 5,116,796 | 5/1992 | Edlund | 502/154 |

Primary Examiner—James H. Reamer
Attorney, Agent, or Firm—Morrison & Foerster

[57] ABSTRACT

This invention is a process for catalytically oxidizing cycloolefins, particularly cyclohexenes, to form a variety of oxygenates. The catalyst used in the process is a covalently bonded iridium-heteropolyanion species. The process uses the catalyst in conjunction with a gaseous oxygen containing gas to form 2-cyclohexen-1-ol and also 2-cyclohexen-1-one.

14 Claims, 5 Drawing Sheets

PROCESS FOR CATALYTICALLY OXIDIZING CYCLOOLEFINS, PARTICULARLY CYCLOHEXENE

FIELD OF THE INVENTION

This invention is a process for catalytically oxidizing cycloolefins, particularly cyclohexenes, to form a variety of oxygenates. The catalyst used in the process is a covalently bonded iridium-heteropolyanion species. The process uses the catalyst in conjunction with a gaseous oxygen containing gas to form 2-cyclohexen-1-ol and also 2-cyclohexen-1-one.

BACKGROUND OF THE INVENTION

Catalytic processes using heterogeneous, bulk, oxide-supported catalysts are notoriously well known. They form the backbone of much of today's chemical industry. However, although these catalyst systems are exceptionally flexible in that they often produce high catalytic turnover rates and their use result in processes in which the catalyst is easily separable from the feed and products, the actual chemical composition of the active sites often remains a mystery. The mechanistic activities at those catalytic sites are similarly difficult to determine. Attempts to circumvent these shortcomings have primarily focused on chemically binding discreet, well-characterized, metallic or organometallic complexes to a support, typically polymer or silicious substrate, thereby making previously soluble organometallic complexes insoluble and atomically dispersed. However, the usefulness of these "heterogenized" complexes as catalysts is limited by the same analytical difficulties associated with characterizing in doing mechanistic studies on bulk solid, two-phase systems.

This invention represents the first example of organic solvent-soluble, atomically dispersed, oxide-supported catalyst precursors, using covalently-bonded iridium-heteropolyanions to oxidize cycloolefins to produce oxygenates.

Certain of these oxygenation catalyst precursors have been disclosed in U.S. patent Ser. No. 020,122, filed Feb. 27, 1987 now abandoned, and its continuation-in-part, Ser. No. 07/275,105, filed Oct. 26, 1988 now U.S. Pat. No. 5,116,796. The earlier applications did not suggest the use of these materials as oxidation catalysts.

SUMMARY OF THE INVENTION

This invention is a process for oxidizing cycloolefins in the liquid phase using gaseous oxygen and a catalyst precursor comprising (in their ionic form) by:

$$[L_n Ir^{(I)}.X_2 M_{15}'_3 O_{62}]^{y-} \quad (I)$$

or by:

$$[L_n Ir^{(I)}.X M_9 M'_3 O_{40}]^{y-} \quad (II)$$

where L is a ligand selected from 1, 5-cyclooctadiene (COD), ethylene, cyclooctene, norbornadiene, and other olefinic ligands, benzene, and similar aryenes, and where "n" is 1 or 2 to satisfy the stoichiometry of the material, X is the "hetero" atom chosen from B, Si, Ge, P, As, Se, Te, I, Co, Mn, and Cu. M is either W or Mo. M' is preferably V, Nb or Ta, but Ti, Zr, and Hf are also useful. Y denotes the ionic charge which is easily calculated once the various atoms in the molecule are known. The preferred ionic species is:

$$[A^{+8}][LnIr.P_2W_{15}Nb_3O_{62}]^{-8}. \quad (III)$$

The preferred species is prepared by reacting under nitrogen $$[(n\text{-}C_4H_9)_4N]_9 P_2 W_{15} Nb_3 O_{62} \quad (IV)$$

either with $$[(1,5\text{-}COD)MCl]_2 \quad M\text{-}Ir, Rh \quad (V)$$

or $$[Ir(COD)(CH_3CN)_2]BF_4 \quad (VI)$$

The products are highly oxygen-sensitive and require the presence of nitrogen, argon or another suitable inert gas to reach the desired products. The preferred catalyst precursor made in this way is:

$$[n\text{-}C_4H_9)_4N]_5 Na_3(1,5\text{-}COD)Ir\text{-}P_2 W_{15} Nb_3 O_{62}] \quad (VII)$$

The process involves contacting cycloolefins and oxygen with the dissolved catalyst. The oxygenate products are soluble in reaction medium and may be easily removed therefrom by known techniques.

DETAILED DESCRIPTION OF THE INVENTION

Figure 1:
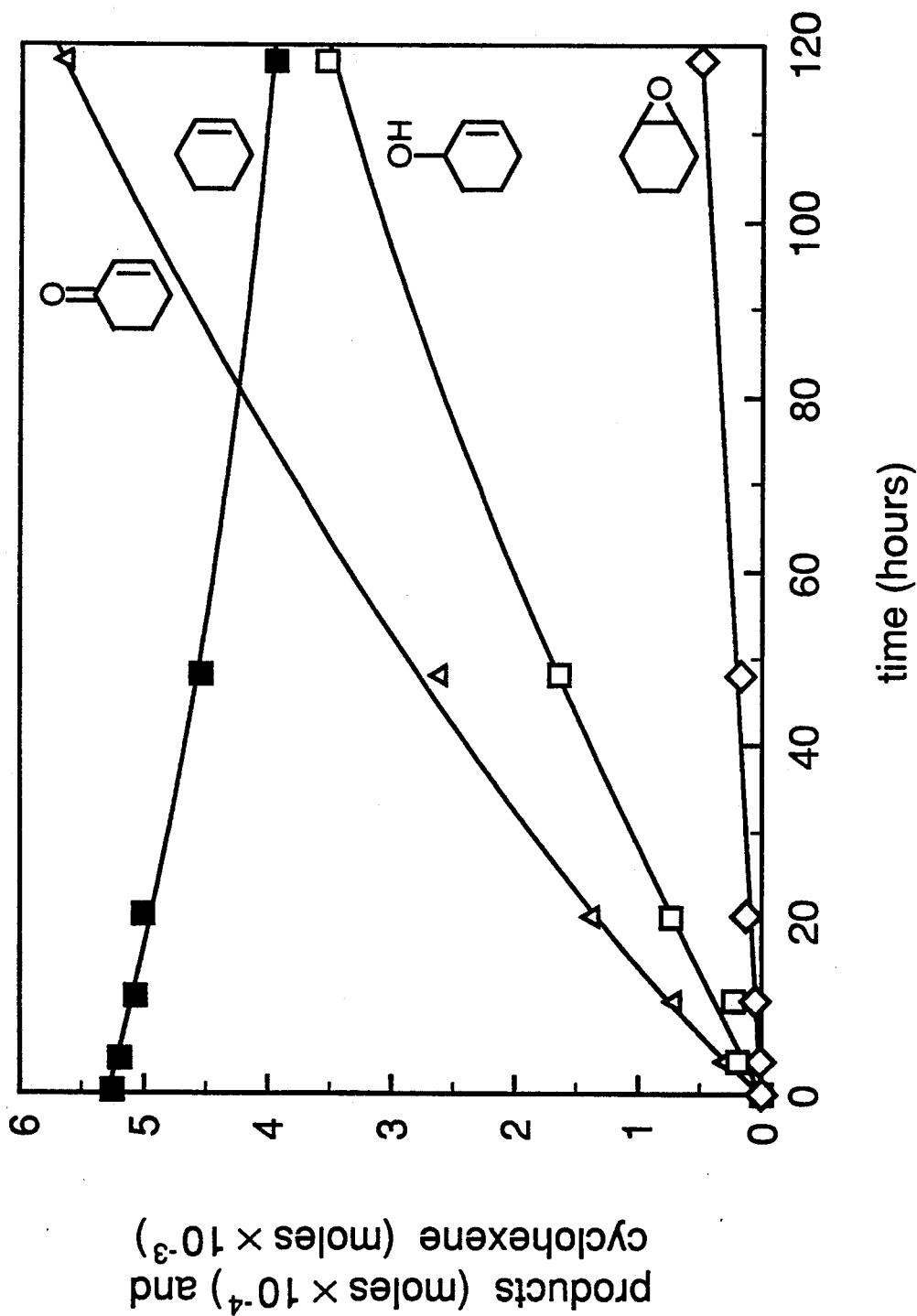
FIG. 1 shows a time plot of the yield of certain oxygenated products as a function of time.

In aqueous solutions certain metal oxides undergo stepwise hydrolysis-oligomerization reactions upon acidification according to the following representative stoichiometries ["Heteropoly and Isopoly Oxometalates" by M. T. Pope (Springer-Verlag, N.Y., 1983):

$$2aH^+ + bMO_n^{-r} \rightarrow [M_b O_y]^{-p} + a H_2O \quad (1)$$
where $bn = y + a$ (oxygen atom balance)
$br - 2a = p$ (charge balance)

$$2aH^+ + bMO_n^{-r} + cXO_q^{-s} \rightarrow [X_c M_b O_y]^{-p} + aH_2O \quad (2)$$
where $bn + cq = y + a$ (oxygen atom balance)
$br + cs - 2a = p$ (charge balance)

and where M can be one of several metals, e.g., W, Mo, V, or mixtures of these metals. X is usually P or Si but can be a number of other elements. The condensed metal oxides, e.g., $[X_c M_b O_y]^{-p}$, form a symmetric three-dimensional array whose structure, composition, and properties can vary a great deal with various X and M elements. Which structure is present depends on the acidity of the solution, the initial amounts of $MO_n^{-r}$ and $XO_q^{-s}$, and other reaction conditions. In some cases, even under the same reaction conditions, different structures may be present. Products formed by reaction (1) are called isopolyoxoanions. Products formed by reaction (2) contain a "hetero" atom X, usually centrally located in the structure, and as a result these products are referred to as heteropolyoxoanions.

Catalysis via polyoxoanion supported (covalently bonded) transition metals has heretofore gone largely unrecognized despite the potential such compounds represent in terms of a new class of atomically dispersed oxide-supported catalysts. It is important here to appreciate the distinction between transition metals supported on a polyoxoanion, as opposed to a metal incorporated into a polyoxoanion. By polyoxoanion supported metals we mean species that are firmly attached to a $K_3$—O site of surface oxygens of a polyoxoanion analogous to the envisioned situation of at least some oxide-supported heterogeneous catalysts. This situation is quite different from the more common one of metals or organometallics incorporated into a vacancy in the polyoxoanion framework by four, approximately square-planar oxide ligands, e.g., $CpTi^{+3}$ incorporated into $PW_{11}O_{39}^{7-}$ or $Mo_5O_{18}^{6-}$ as $PW_{11}O_{39}(CpTi)^{4-}$ and $Mo_5O_{18}(CpTi)^{3-}$, respectively, or the incorporated $Nb^{+5}$ in $NbW_5O_{19}^{3-}$, $Nb_2W_4O_{19}^{4-}$, or $SiW_9Nb_3O_{40}^{7-}$. Metals supported on a polyoxoanion surface (but not incorporated metals) can have cis-coordination sites, greater coordinative unsaturation, and perhaps mobility on the oxide surface, all leading to reactions and mechanisms unavailable to incorporated metals and thus to distinctive catalytic chemistries. Also worth distinguishing here are organometallics bound by a single, labile bridging oxygen, cases where the polyoxoanion behaves like a simple alkoxide, RO—, e.g., RO—U(Cp)$_3$—OR (OR=—OMW$_5$O$_{19}^{3-}$; M=Ta$^{5+}$, Nb$^{5+}$)$_3$ rather than as a tight binding, $K_3$—O ligand or support.

Two key experimental tests of a tightly and covalently polyoxoanion supported metal cation are: 1) whether the metal will be rapidly reduced to $M^{(0)}$ under H$_2$; 2) whether a cation exchange resin will remove the metal from contact with the polyoxoanion; or 3) direct $^{17}$O NMR detection of polyoxoanion oxygen-supported metal bonds (such as Nb-O-Ir). By these tests the Ir-$^{(I)}$.[P$_2$W$_{15}$Nb$_3$O$_{62}^{9-}$] disclosed herein is covalently bonded, while RhCl(PPh$_3$)$_3$+SiW$_{12}$O$_{40}^{4-}$ or SiMo$_1$.$_2$O$_{40}^{4-}$ is clearly not covalently bonded.

For purposes of brevity in the specification, the preferred catalytic species of the present invention, $X^{+8}[L'_nIr.P_2W_{15}Nb_3O_{62}]^{-8}$ will hereinafter be referred to as the iridium mixed phosphotungstate complex.

The compounds which constitute the present invention are polyoxoanion supported metal complexes. As is well known in the art, heteropolyanions include either Dawson or Keggin structures. The precursor of the species used in the instant invention is a Dawson structure polyoxoanion represented by the following formula:

$$[L_nIr^{(I)}.X_2M_{15}M'_3O_{62}]^{x-} \quad (4)$$

In this formula, L is an olefinic ligand, preferably chosen from the group consisting of 1,5-cyclooctadiene (COD), cyclooctene, norbornadiene and ethylene; n is 1 or 2, depending upon the number of available electron pairs within the ligand. X is the "hetero" atom chosen from the group consisting of B, Si, Ge, P, As, Se, Te, I, Co, Mn and Cu. M is W or Mo. M' is preferably Nb or V, but may also be chosen from the group consisting of Ti, Zr, Ta or Hf. y denotes the ionic charge of the composition which is easily calculated by one of ordinary skill in the art once the various atoms in the molecule are known.

The countercation for the polyoxoanion supported metal complex is chosen from two broad categories of cations. One preferred countercation is tetraalkyl ammonium, preferably tetrabutyl ammonium. The second group of countercations consists of alkali metals chosen from the group consisting of Na$^+$, K$^+$, Rb$^+$, and Cs$^+$. Other cations are possible, including di- or higher valency cations.

The compositions have demonstrated specific utility in the catalytic oxygenation of olefins in the liquid phase.

The process is carried out by dissolving the catalyst in suitable solvent, e.g., dichloromethane, 1,2-dichloroethane, acetone, acetonitrile, N,N,-dimethylacetamide, and dimethylsulfoxide, and mixed with the cycloolefin, e.g., cyclohexene. The mixture is then contacted with an oxygen-containing gas at an appropriate temperature. We have found that typical temperatures may be between $-50°$ C. and $100°$ C. The contact with the oxygen-containing gas may be accomplished using known reaction engineering techniques. For instance, stirring to promote the area of liquid gas interface is desirable. The product oxygenates are dissolved in the solvent and can be removed using known techniques. We have not observed active oxidant products (peroxides such as cyclohexene hydroperoxide). We have additionally found that hydrogen peroxide may be used in place of molecular oxygen as may an H$_2$/O$_2$ mixture (under non-explosive conditions).

EXAMPLES

Example 1

A sample of the catalyst [[n-C$_4$H$_9$)$_4$N]$_5$Na$_3$(1,5-COD)Ir.P$_2$W$_{15}$Nb$_3$O$_{62}$] (formula VII) was prepared in a dry box having less than 1 part per million oxygen concentration using a process disclosed in: "Polyoxoanions as Soluble Metal Oxide Analogs," Finke et al., *Inorganic Chemistry*, vol. 29, no. 10, pp. 1784–1787, 1990. The catalyst precursor [(n-C$_4$Ha)$_4$N]$_9$P$_2$W$_{15}$Nb$_3$O$_{62}$ (formula IV) was dissolved in a variety of solvents (dichloromethane, 1,2-dichloroethane, acetone, acetonitrile, N,N-dimethyl acid amide, and dimethylsulfoxide). These solvents were distilled from either calcium hydride or potassium carbonate under dry nitrogen or under a partial vacuum. The cyclohexene used in the oxidation reaction was distilled from sodium under dry nitrogen. After distillation, the liquids were dispensed into glassware that had been thoroughly cleansed, dried at 200° C., and cooled under a nitrogen flow. The solvents were stored in a dry box during the simplified process.

Example 2

A similar material [(n-C$_4$H$_9$)$_4$N]$_5$Na$_3$(1,5-COD)Rh.P$_2$W$_{15}$Nb$_3$O$_{62}$] was similarly prepared from [(n-C$_4$Ha)$_4$N]$_9$P$_2$W$_{15}$Nb$_3$O$_{62}$ and [(1,5-COD)IrCl]$_2$ M-Ir, Rh where the metal in the formula is Rh.

Example 3

Another similar material [(n-C$_4$H$_9$)$_4$N]$_4$Na$_3$(C$_6$H$_6$)Ru.P$_2$W$_{15}$Nb$_3$O$_{62}$] was prepared using [(n-C$_4$Ha)$_4$N]$_9$P$_2$W$_{15}$Nb$_3$O$_{62}$ and [(C$_6$H$_6$) RuCl$_2$]$_2$.

Example 4

Each of the three catalysts from Examples 1, 2 and 3 was used for the oxidation of cyclohexene using molecular oxygen. Additionally, as controls, the materials used as catalyst constituents, [(n-$C_4H_9)_4N]_9P_2W_{15}Nb_3O_{62}$ and formula [(1,5-COD)IrCl$_2$] M-Ir, Rh were examined. In a dry box, the respective materials (25 mg, $4.41 \times 10^{-3}$ mmol) was dissolved in a sealable glass vial (16 or 100 ml) containing a magnetic stir bar and 3 ml of the appropriate solvent. Cyclohexene (0.5 ml, 4.94 mmol) was added to the solution, the vials sealed, and brought immediately out of the dry box. The glass vial was then attached to a vacuum line, cooled to 77° K. (liquid nitrogen trap) and degassed by three freeze/pump/thaw cycles. The vial was allowed to warm to 195° K. (dry ice/ethanol bath) and 1 atmosphere of oxygen gas was introduced to the system. The vial was then placed in a 38° C. bath and vigorously stirred. The vial was removed from the bath every 4 hours to refill the tube with 1 atmosphere of oxygen. The reaction column was periodically sampled by syringe and analyzed by gas chromatography on a carbowax capillary column. The amount of each product was calculated by comparison to a calibration curve for known materials (under identical conditions). Tests for active oxygen products, for example peroxide such as cyclohexane hydroperoxide, by iodometry (see, Fine et al., *J. Organomet. Chem.* 22:219 (1970)) proved negative (less than or equal to $1 \times 10^{-6}$ mol in CH$_2$Cl$_2$).

Figure 2:
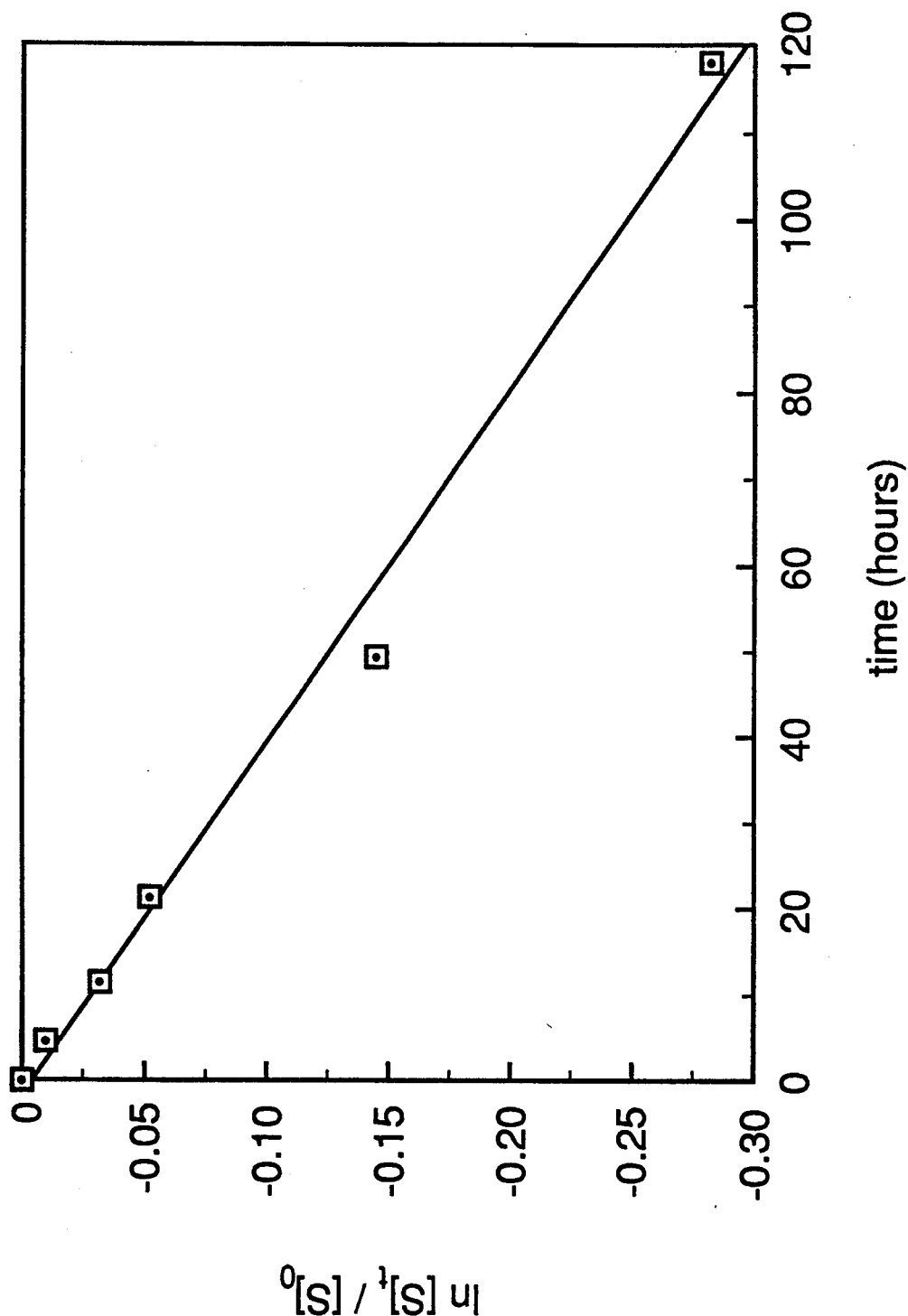
FIG. 2 is a plot of the rate of cyclohexene oxygenation in the presence of a highly desired catalyst as a function of time.
Figure 3:
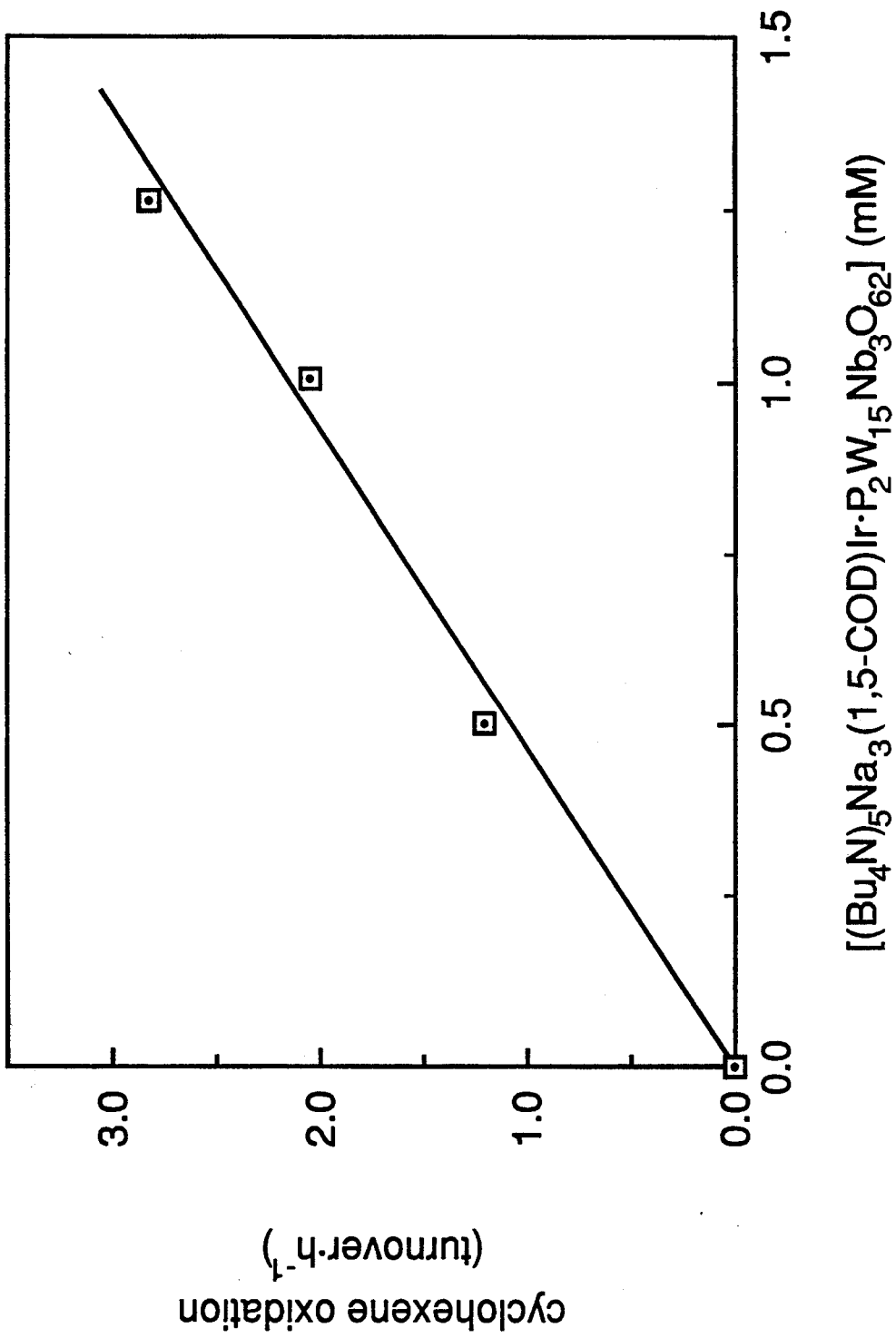
FIG. 3 is a plot of cyclohexene oxidation as a function of the concentration of catalyst in an example.
Figure 4:
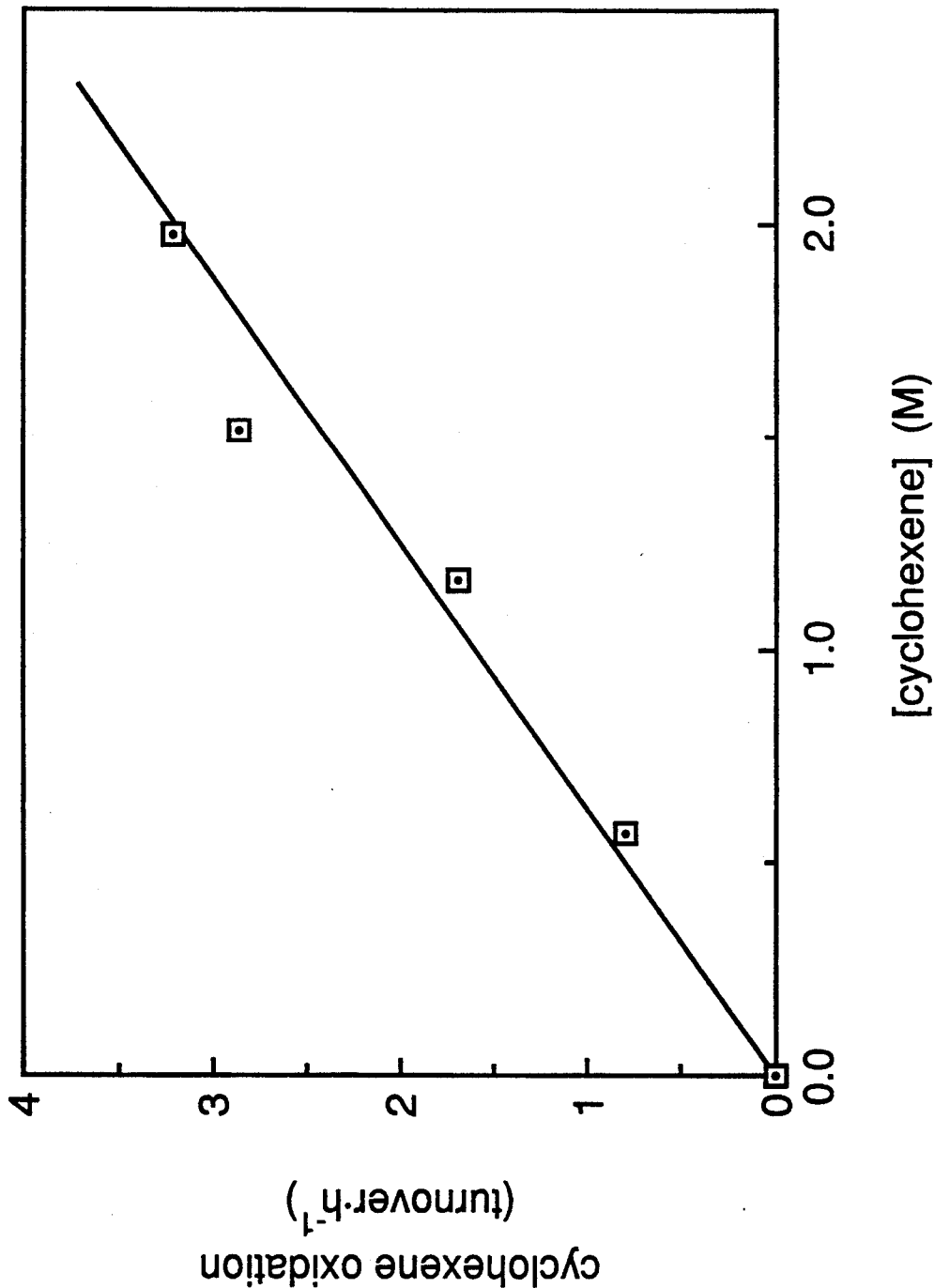
FIG. 4 is a plot of cyclohexene oxidation as a function of concentration of cyclohexene.
Figure 5:
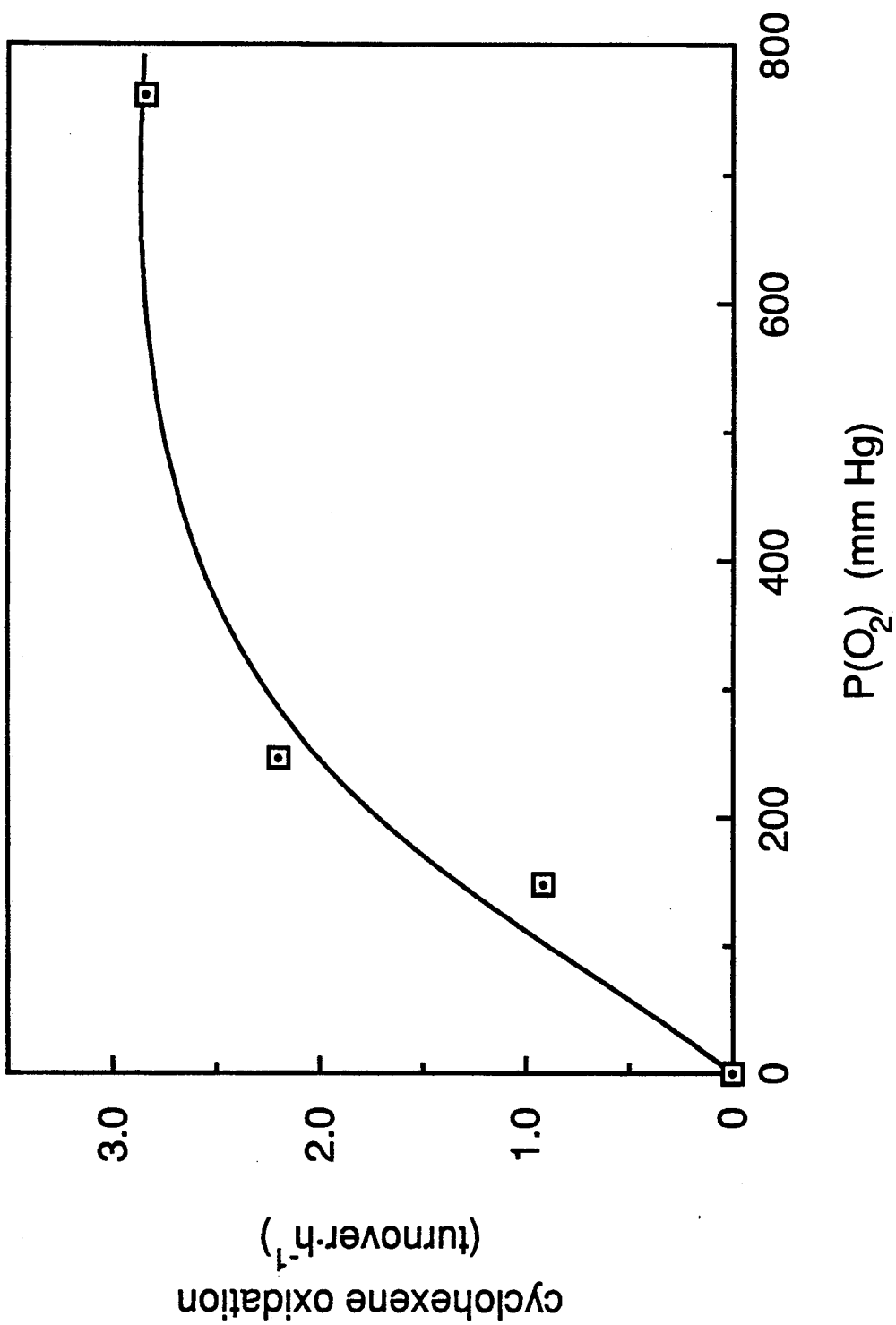
FIG. 5 is a plot of cyclohexene oxidation as a function of the pressure of oxygen.

The products of cyclohexene oxidation, in the presence of the Example 1 catalyst and oxygen, and under conditions of low cyclohexene conversion, is shown in FIG. 1, during which time the yellow-brown solution deepened in color and remained visibly homogenous. After the reaction had been allowed to proceed for 118 hours, a small amount of precipitated catalyst was observed. This apparently was due to the catalyst's insolubility in the water formed during the reaction period. The ratio of the primary products, 2-cyclohexen-1-ol and 2-cyclohexane-1-one, show little change with time and the total number of turnovers after 330 hours is approximately 450. Preliminary kinetic studies indicated that the rate of decrease of cyclohexene $-d[cyclohexene]/dt = K_{2(observed)}$ [[n-C$_4$H$_9$)$_4$N]$_5$Na$_3$(1,5-COD)Ir.P$_2$W$_{15}$Nb$_3$O$_{62}$]$^1$[P(O$_2$)]$^{1\to0}$ is in the concentration ranges of the catalyst between $1.3 \times 10^{-3}$ and $4.0 \times 10^{-3}$M, and cyclohexene from 0 to 2M, and a pressure of (P[O$_2$]) between 0 and 760 mm of mercury, respectively. Saturation kinetics appeared to be attained at partial pressure of 760 mm of mercury. FIG. 2 shows that the first-order plots of cyclohexene disappearance show good linearity. The initial turnover frequency (TOF)$_i$, which was calculated from the slope of the first order plots and normalized to the concentration of the catalyst, yielded (TOF)$_I$=2.9 h$^{-1}$ at 38° C. This value is larger than those values reported for Ir(CO)(PPh$_3$)$_2$Cl(O$_2$) @0.39 h$^{-1}$ and 65° C., Collman et al., *J. Am. Chem. Soc.* 89:4809 (1967); Ir(CO)(PPh$_3$)$_2$Cl(O$_2$) @0.44 h$^{-1}$ and 65° C., in Fusi et al., *J. Organomet. Chem.* 26:417 (1971); and [IrHCl$_2$Cl,5-(OD)]$_2$ @ 0.08 h$^{-1}$ and 5° C., see Atlay et al., *Can. J. Chem.* 61.1332 (1983).

The catalytic oxygenation of cyclohexene in the presence of various catalysts and oxygen was performed. From these tests, it was found that the activity of [(n-C$_4$H$_8$)$_4$N]$_9$P$_2$W$_{15}$Nb$_3$O$_{62}$-supported Ir, Rh, and Ru compounds decreased as follows:

[[n-C$_4$H$_9$)$_4$N]$_5$Na$_3$(1,5-COD)Ir.P$_2$W$_{15}$Nb$_3$O$_{62}$](most active)
[(n-C$_4$H$_9$)$_4$N]$_4$Na$_3$(C$_6$H$_6$)Ru.P$_2$W$_{15}$Nb$_3$O$_{62}$]

-continued
[(n-C$_4$H$_9$)$_4$N]$_5$Na$_3$(1,5-COD)Rh.P$_2$W$_{15}$Nb$_3$O$_{62}$](least active).

The activity of oxygenation by the [[n-C$_4$H$_9$)$_4$N]$_5$Na$_3$(1,5-COD)Ir.P$_2$W$_{15}$Nb$_3$O$_{62}$] relative to its precursor materials [(1,5.COD)IrCl]$_2$, and the control (no iridium) of the [(n-C$_4$H$_8$)$_4$N]$_9$P$_2$W$_{15}$Nb$_3$O$_{62}$ are 100:1 and 100:0, respectively. The product selectivity did not change significantly in this series. The selectivities are similar to those observed for hydrogen peroxide under identical conditions. The catalytic oxygenation reaction was enhanced by use of an oxygen/hydrogen system.

The oxygenation of cyclohexene with gaseous oxygen in the presence of the preferred catalyst precursor [[n-C$_4$H$_9$)$_4$N]$_5$Na$_3$(1,5-COD)Ir.P$_2$W$_{15}$Hb$_3$O$_{62}$] was performed. From this test it was found that the rate constants for oxidation are solvent-dependent, decreasing as follows: CH$_2$Cl$_2$>1,2-dichloroethane>acetone>acetonitrile>N,N-dimethylacid amide=dimethyl sulfoxide, with relative rates of 6:4.25:2.75:1:0:0, respectively. In all solvents, the primary products were 2-cyclohexen-1-ol and 2-cyclohexen-1-one. The carbon/mass balance in these examples was >85%.

We claim as our invention:

1. A process for the oxidation of cyclohexene comprising the steps of:
    contacting a cyclohexene-containing solution with a solvent containing a dissolved catalyst, the catalyst comprising a cation and anion where the anion has the following formula:

where L is an olefinic ligand,
    n is 1 or 2,
    X is selected from B, Si, Ge, P, As, Se, Te, I, Co, Mn, and Cu,
    M is W or Mo,
    M' is Nb or V, and
    y is the resulting ionic charge; and
    contacting the resulting mixture with gaseous oxygen so as to produce oxygenated cyclohexene.

2. The process of claim 1 where the olefinic ligand is selected from 1,5-cyclooctadine, cyclooctene, norbornadiene, and ethylene.

3. The process of claim 1 where the olefinic ligand is 1,5-cyclooctadene.

4. The process of claim 1 where X is P.

5. The process of claim 3 where X is P.

6. The process of claim 1 where M is W.

7. The process of claim 3 where M is W.

8. The process of claim 7 where M' is Nb.

9. The process of claim 1 where the oxygenated cyclohexene comprises 2-cyclohexene-1-ol and 2-cyclohexen-1-one.

10. The process of claim 1 where the solvent is selected from CH$_2$Cl$_2$, 1,2-dichloroethane, acetone, acetonitrile, N,N-dimethylacetamide, or dimethylsulfoxide.

11. The process of claim 1 in which the cation is a tetraalkyl ammonium.

12. The process of claim 11 in which the tetraalkyl ammonium is tetrabutyl ammonium.

13. The process of claim 1 in which the cation is an alkali metal chosen from the group consisting of Na$^+$, K$^+$, Rb$^+$, and Cs$^+$.

14. The process of claim 1 where the mixture is contacted with an oxygen-containing gas at a temperature between $-50°$ C. and $100°$ C.

* * * * *